US012784198B2

United States Patent

(12) United States Patent
Sekimoto et al.

(10) Patent No.: US 12,784,198 B2
(45) Date of Patent: Nov. 3, 2026

(54) EXAMINATION SUPPORT DEVICE, EXAMINATION SUPPORT METHOD, AND STORAGE MEDIUM STORING EXAMINATION SUPPORT PROGRAM

(71) Applicant: AI Medical Service Inc., Tokyo (JP)

(72) Inventors: Hiroyuki Sekimoto, Tokyo (JP); Kaho Akiyoshi, Tokyo (JP)

(73) Assignee: AI Medical Service Inc., Tokyo (JP)

( * ) Notice: Subject to any disclaimer, the term of this patent is extended or adjusted under 35 U.S.C. 154(b) by 322 days.

(21) Appl. No.: 18/508,212

(22) Filed: Nov. 13, 2023

(65) Prior Publication Data

US 2024/0095917 A1 Mar. 21, 2024

Related U.S. Application Data

(63) Continuation of application No. PCT/JP2022/025111, filed on Jun. 23, 2022.

(30) Foreign Application Priority Data

Jun. 24, 2021 (JP) ................................ 2021-104550

(51) Int. Cl.
*G06T 7/00* (2017.01)
*A61B 1/00* (2006.01)
(Continued)

(52) U.S. Cl.
CPC .......... *G06T 7/0012* (2013.01); *A61B 1/0002* (2013.01); *A61B 1/0004* (2022.02); (Continued)

(58) Field of Classification Search
CPC ......... G06T 7/0012; G06T 2207/10068; G06T 2207/20076; G06T 2207/20081; (Continued)

(56) References Cited

U.S. PATENT DOCUMENTS 6,058,322 A * 5/2000 Nishikawa ............ G06T 7/0012 382/128
9,418,419 B2 * 8/2016 Nufer ..................... G16H 30/20
(Continued)

FOREIGN PATENT DOCUMENTS

| | | | |
|---|---|---|---|
| JP | 2019-042156 | A | 3/2019 |
| WO | 2020/166247 | A1 | 8/2020 |
| WO | 2021/029292 | A1 | 2/2021 |

*Primary Examiner* — Anhtuan T Nguyen
*Assistant Examiner* — Shankar Raj Ghimire
(74) *Attorney, Agent, or Firm* — PROCOPIO, CORY, HARGREAVES & SAVITCH LLP

(57) ABSTRACT

There is provided an examination support device that is used by being connected to an endoscope system including a camera unit for being inserted into an inside of a body of a subject, the examination support device including: an acquisition unit for sequentially acquiring a captured image that is captured by the camera unit; a diagnosis unit for performing diagnosis of the inside of the body based on the captured image; a display unit for displaying a diagnosis result that is output by the diagnosis unit; a reception unit for receiving, from a user, selection of an on mode in which the diagnosis result is displayed on the display unit or an off mode in which display is not performed; and a control unit for causing the diagnosis result to be displayed on the display unit in real time in a case where selection of the on mode is received by the reception unit, and causing the diagnosis result to be stored in a storage unit without being displayed on the display unit at least while examination of the inside of the body by the camera unit is being performed, in a case where selection of the off mode is received.

20 Claims, 12 Drawing Sheets

(51) Int. Cl.
*A61B 1/05* (2006.01)
*H04N 23/50* (2023.01)

(52) U.S. Cl.
CPC ............ *A61B 1/00045* (2013.01); *A61B 1/05* (2013.01); *H04N 23/555* (2023.01); *G06T 2207/10068* (2013.01); *G06T 2207/20076* (2013.01); *G06T 2207/20081* (2013.01); *G06T 2207/30096* (2013.01)

(58) Field of Classification Search
CPC ............. G06T 2207/30096; G06T 7/00; A61B 1/0002; A61B 1/00045; A61B 1/05; A61B 1/000094; A61B 1/000096; A61B 1/0005; G06V 10/945; G06V 2201/03
See application file for complete search history.

(56) References Cited

U.S. PATENT DOCUMENTS 11,600,385 B2 * 3/2023 Meguro ........... A61B 1/000096
11,633,084 B2 * 4/2023 Hirasawa .............. G06T 7/0012 382/128
2008/0039692 A1 * 2/2008 Hirakawa .......... A61B 1/00045 600/160
2009/0051695 A1 * 2/2009 Matsuda ............... G06T 7/0012 345/556
2013/0006109 A1 * 1/2013 Takei ................... A61B 1/0646 600/432
2015/0302583 A1 * 10/2015 Jeon ...................... G06T 7/0016 382/128
2019/0073768 A1 3/2019 Shigeta
2019/0117055 A1 * 4/2019 Ito ...................... G02B 23/2461
2019/0287240 A1 * 9/2019 Gaire .................... G06T 7/0012
2020/0008653 A1 * 1/2020 Kamon .............. A61B 1/00055
2020/0113505 A1 * 4/2020 Clingman ............ A61B 5/0095
2020/0320701 A1 * 10/2020 Xiao ...................... G16H 50/20
2021/0113172 A1 * 4/2021 Huang ...................... G06T 1/20
2021/0118550 A1 * 4/2021 Rahman ................ G06T 7/0014
2021/0204794 A1 * 7/2021 Yumbe ................... H04N 7/183
2021/0307725 A1 * 10/2021 Namiki .................. G16H 40/63
2022/0133214 A1 5/2022 Shino
2022/0151462 A1 5/2022 Usuda
2022/0405622 A1 * 12/2022 Nonaka .................. G06N 20/00
2023/0380660 A1 * 11/2023 Iwane ................ A61B 1/00006
2024/0049944 A1 * 2/2024 Kobayashi ............. A61B 5/489
2024/0268627 A1 * 8/2024 Chung ............. A61B 1/000096
2024/0312019 A1 * 9/2024 Higa ..................... G06T 7/0012

* cited by examiner

ON MODE

OFF MODE
(BACKGROUND MODE)

OFF MODE
(COMPLETE OFF MODE)

EXAMINATION SUPPORT DEVICE, EXAMINATION SUPPORT METHOD, AND STORAGE MEDIUM STORING EXAMINATION SUPPORT PROGRAM

CROSS REFERENCE TO RELATED APPLICATION

The present application is based upon and claims the benefit of priority from Japanese Patent Application No. 2021-104550, filed on Jun. 24, 2021, and International application No. PCT/JP2022/025111 filed on Jun. 23, 2022, the entire contents of which are hereby incorporated by reference.

TECHNICAL FIELD

The present invention relates to an examination support device, an examination support method, and an examination support program.

BACKGROUND ART

There is known an endoscope system that captures an inside of a stomach, for example, of a subject by an endoscope and that displays an image of it on a monitor. These days, examination support devices that analyze an image captured by an endoscope system and that notify a doctor of a result of it are becoming widespread (for example, see Patent Literature 1). Furthermore, a mode of use according to which an examination support device is connected to an endoscope system and the examination support device is caused to analyze in real time an in-body image that is captured by the endoscope system is also reaching practical levels.

CITATION LIST

Patent Literature

Patent Literature 1: Japanese Patent Laid-Open No. 2019-42156

SUMMARY OF INVENTION

Technical Problem

If an examination is performed while a diagnosis result calculated by an examination support device is displayed on a display unit, a doctor enjoys an advantage that observation can be performed while focusing on a specific part according to the diagnosis result that is displayed, for example. On the other hand, there is also a case where display of a diagnosis result which takes some time to be displayed is desired to be turned off due to a demand to reduce an examination time when an endoscope is inserted inside the body of a subject, for example. However, if a diagnosis function is completely turned off, a risk of overlooking a lesion is increased.

The present invention has been made to solve problems as described above, and is aimed at providing an examination support device and the like for preventing a lesion from being overlooked while allowing switching of display according to a state of an examination.

Solution to Problem

An examination support device according to a first mode of the present invention is an examination support device that is used by being connected to an endoscope system including a camera unit for being inserted into an inside of a body of a subject, the examination support device including: an acquisition unit for sequentially acquiring a captured image that is captured by the camera unit; a diagnosis unit for performing diagnosis of the inside of the body based on the captured image; a display unit for displaying a diagnosis result that is output by the diagnosis unit; a reception unit for receiving, from a user, selection of an on mode in which the diagnosis result is displayed on the display unit or an off mode in which display is not performed; and a control unit for causing the diagnosis result to be displayed on the display unit in real time in a case where selection of the on mode is received by the reception unit, and causing the diagnosis result to be stored in a storage unit without being displayed on the display unit at least while examination of the inside of the body by the camera unit is being performed, in a case where selection of the off mode is received.

An examination support method according to a second mode of the present invention is an examination support method performed using an examination support device that is used by being connected to an endoscope system including a camera unit for being inserted into an inside of a body of a subject, the examination support method including: a reception step of receiving, from a user, selection of an on mode in which a diagnosis result is displayed on a display unit or an off mode in which display is not performed; an acquisition step of sequentially acquiring a captured image that is captured by the camera unit; a diagnosis step of performing diagnosis of the inside of the body based on the captured image; a display control step of causing the diagnosis result to be displayed in real time on the display unit in a case where selection of the on mode is received in the reception step; and a storage control step of causing the diagnosis result to be stored in a storage unit without being displayed on the display unit at least while examination of the inside of the body by the camera unit is being performed, in a case where selection of the off mode is received in the reception step.

A storage medium storing an examination support program according to a third mode of the present invention is a storage medium storing an examination support program for controlling an examination support device that is used by being connected to an endoscope system including a camera unit for being inserted into an inside of a body of a subject, the examination support program being for causing a computer to perform: a reception step of receiving, from a user, selection of an on mode in which a diagnosis result is displayed on a display unit or an off mode in which display is not performed; an acquisition step of sequentially acquiring a captured image that is captured by the camera unit; a diagnosis step of performing diagnosis of the inside of the body based on the captured image; a display control step of causing the diagnosis result to be displayed in real time on the display unit in a case where selection of the on mode is received in the reception step; and a storage control step of causing the diagnosis result to be stored in a storage unit without being displayed on the display unit at least while examination of the inside of the body by the camera unit is being performed, in a case where selection of the off mode is received in the reception step.

Advantageous Effects of Invention

According to the present invention, there may be provided an examination support device and the like for preventing a lesion from being overlooked while allowing switching of display according to a state of an examination.

DESCRIPTION OF EMBODIMENT

Hereinafter, the present invention will be described based on an embodiment of the invention, but the invention according to the claims is not limited to the embodiment described below. Moreover, not all the configurations described in the embodiment are essential as means for solving the problems.

Figure 1:
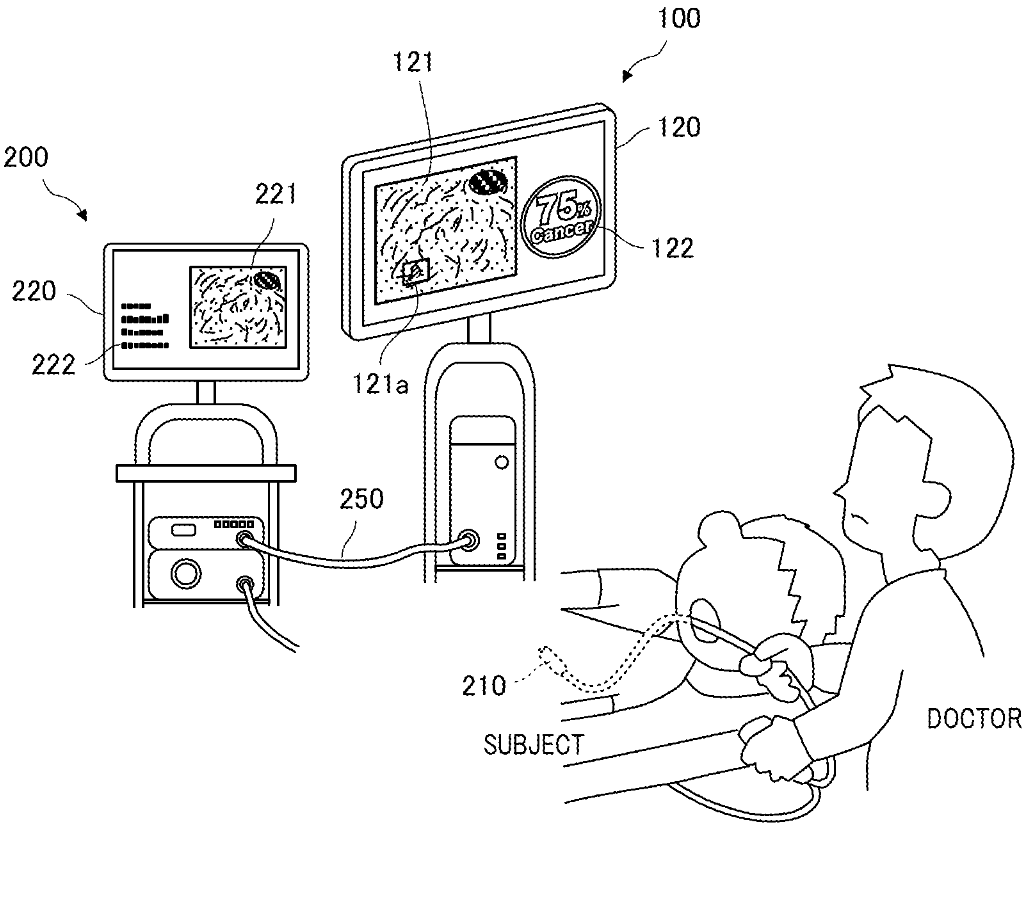
FIG. 1 is a diagram showing a manner of an endoscopic examination performed using an endoscope system and an examination support device according to a present embodiment.

FIG. 1 is a diagram showing a manner of an endoscopic examination performed using an endoscope system 200 and an examination support device 100 according to a present embodiment, and is a diagram that particularly shows the examination support device 100 functioning in an on mode described later. The endoscope system 200 and the examination support device 100 are both installed in a consultation space. The endoscope system 200 includes a camera unit 210, and as shown in the drawing, the camera unit 210 is inserted into an organ, such as a stomach, in a body of a subject who is lying down, through a mouth, and transmits, to a system main body, an image signal of an image that is obtained by capturing an inside of the organ. Insertion of the camera unit 210 into an organ and an image capturing operation are performed by a doctor.

The endoscope system 200 includes a system monitor 220 that is configured by a liquid crystal panel, for example, and processes the image signal transmitted from the camera unit 210 and displays the same as a captured image 221 that can be viewed, on the system monitor 220. Furthermore, the endoscope system 200 displays examination information 222 including subject information, camera information about the camera unit 210, and the like on the system monitor 220.

The examination support device 100 is connected to the endoscope system 200 by a connection cable 250. The endoscope system 200 transmits a display signal that is transmitted to the system monitor 220, also to the examination support device 100 via the connection cable 250. That is, the display signal in the present embodiment is an example of an image signal that is provided to an external device by the endoscope system 200. The examination support device 100 includes, as a display unit, a display monitor 120 that is configured by a liquid crystal panel, for example, and extracts an image signal corresponding to the captured image 221 from the display signal that is transmitted from the endoscope system 200, and sequentially displays the same as a captured image 121 that can be viewed, on the display monitor 120.

In the case where the examination support device 100 is set to the on mode, a doctor performs an examination while viewing the captured image 121 that is displayed in real time according to operation of the camera unit 210. The doctor operates the camera unit 210 such that a target part that is to be diagnosed by the examination support device 100 is displayed as the captured image 121.

In the on mode, for example, when a diagnosis trigger from the doctor is detected, the examination support device 100 generates, from the captured image 121 at the time point, image data that is to be input to a neural network for analysis described later. Then, a diagnosis result that is generated from an output from the neural network for analysis is converted into a computer graphic and is displayed on the display monitor 120 as a CG indicator 122. In the illustrated example, a diagnosis result indicating a 75% probability of being estimated to be cancer is displayed. Furthermore, a region for which such determination is performed is indicated by a diagnosis region frame **121*a* that is superimposed on the captured image 121. The diagnosis result is displayed for a specific period of time, and then, switching to the captured image 121 that is captured by the camera unit 210** in real time is performed.

Figure 2:
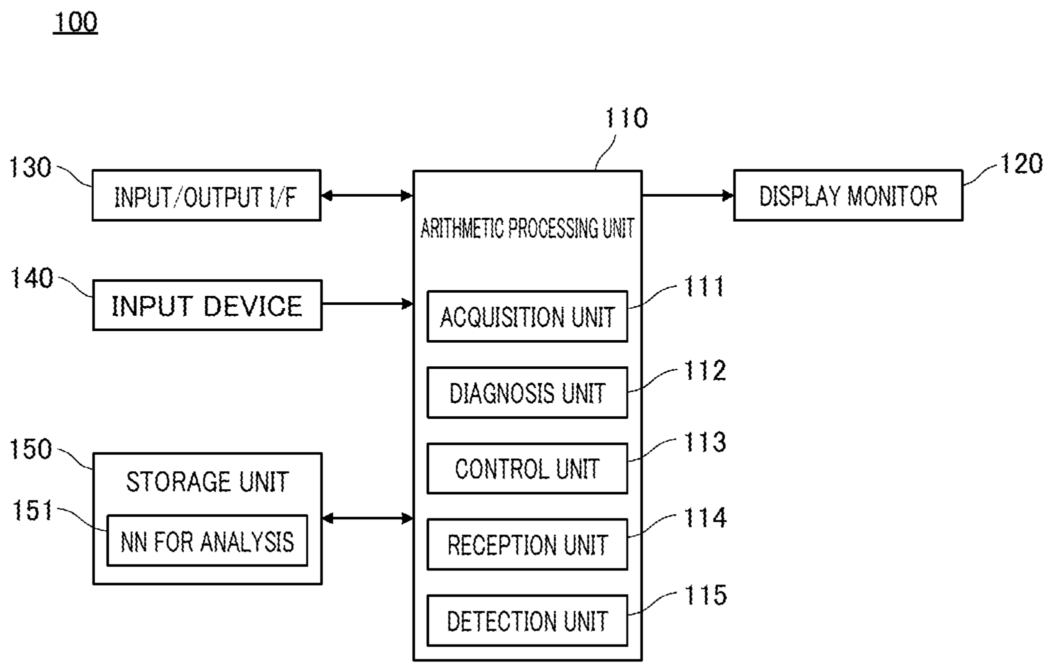
FIG. 2 is a hardware configuration diagram of the examination support device.

FIG. 2 is a hardware configuration diagram of the examination support device 100. The examination support device 100 mainly includes an arithmetic processing unit 110, the display monitor 120, an input/output interface 130, an input device 140, and a storage unit 150. The arithmetic processing unit 110 is a processor (CPU: Central Processing Unit) that performs processes of controlling the examination support device 100 and executing programs. The processor may operate in conjunction with an arithmetic processing chip such as an application specific integrated circuit (ASIC) or a graphics processing unit (GPU). The arithmetic processing unit 110 performs various processes related to supporting of examination by reading out an examination support program that is stored in the storage unit 150.

As described above, the display monitor 120 is a monitor including a liquid crystal panel, for example, and the display monitor 120 displays the captured image 121, the CG indicator 122, and the like in a visible manner. The input/output interface 130 is a connection interface that includes a connector for connecting the connection cable 250, and that is for exchanging information with an external appliance. The input/output interface 130 includes a LAN unit, for example, and takes in the examination support program and update data for a neural network for analysis 151 described later from an external appliance and transfers the same to the arithmetic processing unit 110.

The input device 140 is a keyboard, a mouse, or a touch panel that is superimposed on the display monitor 120, for example, and a doctor or an assistant may operate the same to change settings of the examination support device 100 and to input information necessary for examination.

The storage unit 150 is a non-volatile storage medium, and is configured by a hard disk drive (HDD), for example. The storage unit 150 is capable of storing, in addition to programs for controlling the examination support device 100 and for executing processes, various parameter values to be used for control and calculation, functions, display element data, look-up tables, and the like. In particular, the storage unit 150 stores the neural network for analysis 151. The neural network for analysis 151 is a trained model for calculating, when image data captured by the camera unit 210 is input, a region in the image where a lesion is estimated to be present and an estimated probability of estimating it to be a lesion. Additionally, the storage unit 150 may be configured by a plurality of pieces of hardware, and for example, a storage medium for storing programs, and a storage medium for storing the neural network for analysis 151 may be configured by separate pieces of hardware.

The arithmetic processing unit 110 also serves a role of an arithmetic functional unit that performs various calculations according to processes which the examination support program instructs. The arithmetic processing unit 110 may function as an acquisition unit 111, a diagnosis unit 112, a control unit 113, a reception unit 114, and a detection unit 115. The acquisition unit 111 sequentially acquires display signals that are transmitted from the endoscope system 200, and develops each into a regenerated signal image. Furthermore, an image region indicating a captured image that is captured by the camera unit 210 is established by retrieving a region of change where an amount of difference between successive regenerated signal images is equal to or greater than a reference amount. When the image region is once established, the acquisition unit 111 sequentially generates the captured image 121 as a frame image, from the image region of a display signal that is sequentially acquired thereafter.

The diagnosis unit 112 inputs the captured image 121 as a diagnosis image to the neural network for analysis 151 read from the storage unit 150, and causes a region, in the image, where a lesion is possibly present to be output together with its estimated probability. The diagnosis unit 112 generates a diagnosis result by associating an input image or the like with the output.

The control unit 113 controls display on the display monitor 120 by generating a display signal for a display page, controls reading/writing of data with respect to the storage unit 150, and controls transmission/reception of various control signals to/from an external appliance via the input/output interface 130, for example. In particular, when the on mode is executed, the diagnosis result generated by the diagnosis unit 112 is caused to be displayed in real time on the display monitor 120. When a background mode in the off mode is executed, the diagnosis result generated by the diagnosis unit 112 is stored in the storage unit 150 without being displayed on the display monitor 120 at least while examination of the inside of the body of a subject is being performed.

The reception unit 114 receives selection of the on mode or the off mode from a doctor, who is a user, via the input device 140. The detection unit 115 detects end of examination that is performed by inserting the camera unit 210 inside the body of a subject.

With a conventional examination support device, captured images captured by a camera unit inserted inside the body of a subject are sequentially taken in, and when a diagnosis trigger from a doctor is detected, diagnosis is performed based on the captured image at the time point, and a result of it is immediately displayed. That is, a use mode where a doctor views the diagnosis result in real time according to operation of the camera unit is generally adopted. However, an examination time when the camera unit is inserted inside the body of a subject is desired to be reduced as much as possible depending on a medical condition of the subject, property of the examination, and the like, or more specifically, if the subject is an elderly person, has a pre-existing condition, or taking medicines, for example. In such a case, a time when the camera unit is stopped to provide a diagnosis trigger or a time for a calculation process for calculating the estimated probability of a lesion may not be allowable. In such a case, the examination support device is turned off.

However, when the examination support device is turned off, an original function of supporting diagnosis by the doctor cannot be enjoyed, and a risk of overlooking a lesion is increased. Furthermore, though there is a demand to actively use the examination support device in small- to medium-sized clinics where biopsy often cannot be performed, it becomes impossible to cope with it. Moreover, a simple mistake is also conceivable where the doctor turns off the examination support device in an examination and forgets to turn on the examination support device in the next examination.

Accordingly, the examination support device 100 according to the present embodiment adopts two off modes in addition to the existing on mode. The two off modes are the background mode and a complete off mode, and in an initial setting, switching to the background mode is performed in a case where the off mode is selected by the doctor.

The on mode is a mode of displaying the diagnosis result in real time. Of the off modes, the background mode is a mode of performing a diagnosis process by the diagnosis unit 112, and storing the diagnosis result in the storage unit 150 without displaying the diagnosis result while in-body examination is being performed. Of the off modes, the complete off mode is a mode where the diagnosis process by the diagnosis unit 112 is not performed. Additionally, in the present embodiment, real-time display allows for a delay of a processing time required for image processing or diagnosis processing from real time, and may be immediate display after continuous processes. For example, a case where progress of a process is displayed by displaying a progress bar during the diagnosis process and a diagnosis result of it is immediately displayed after completion of the process is also expressed as real-time display.

Figure 3A:
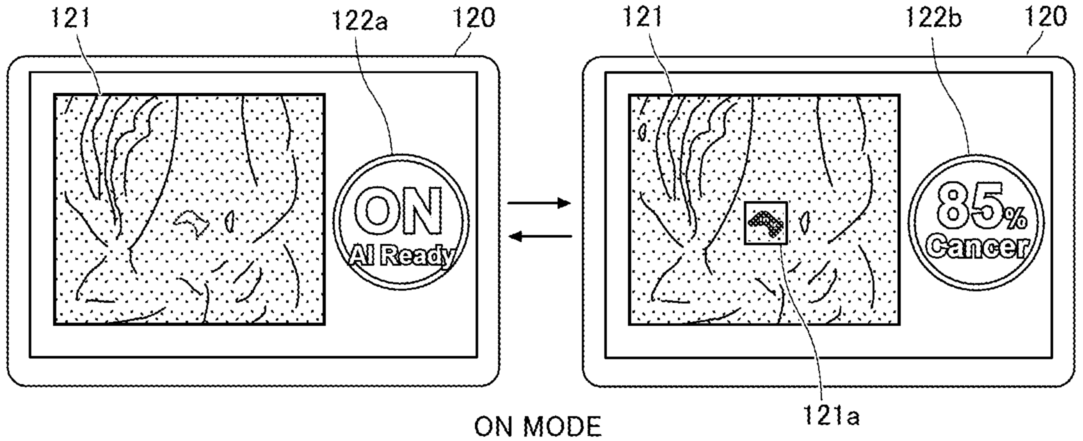
FIG. 3 is a diagram showing an example of a display page in each mode.

FIG. 3 is a diagram showing an example of a display page in each mode. More specifically, each diagram is an example of a display page during an examination when the camera unit 210 is inserted inside the body of the subject. FIG. 3(A) is an example of a display page where the on mode is executed. In the case where the on mode is executed, there are mainly two display states, namely, a standby display state where a captured image captured by the camera unit 210 is displayed in real time, and a result display state where a diagnosis result of performing diagnosis on a specific captured image is displayed.

A left diagram in FIG. 3(A) shows an example of the standby display state. In the standby display state, the captured image 121 that is sequentially updated is arranged on the left, and a standby indicator **122*a* indicating a diagnosis standby state is arranged on the right. The captured image 121 that is sequentially updated adopts so-called live display of displaying the captured image captured by the camera unit 210 with substantially no delay. The standby indicator 122***a* is a computer graphic including "ON" indicating the on mode and a text "AI Ready" indicating the diagnosis standby state, and is one mode of the CG indicator 122. A display mode in such an on mode is referred to as on-mode live display.

A right diagram in FIG. 3(A) shows an example of the result display state. In the result display state, the captured image 121 used as a diagnosis image is arranged on the left, and a result indicator 122*b* indicating the diagnosis result is arranged on the right. The result indicator 122*b* is a computer graphic including a numerical value of the estimated probability of being estimated to be a lesion ("85%" in the example in the diagram), and a text indicating a type of the lesion ("Cancer" in the example in the diagram), and is one mode of the CG indicator 122. Furthermore, the diagnosis region frame 121*a* is superimposed on the captured image 121 so that a region that is estimated to be the lesion can be grasped. The result display state continues for a specific period of time (such as two seconds), and then, display returns to the diagnosis standby state.

Figure 3B:
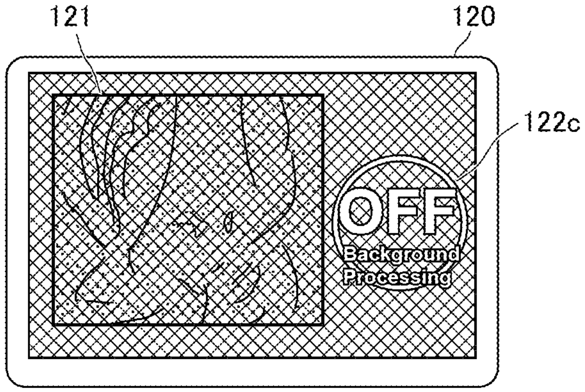

FIG. 3(B) is an example of a display page where the background mode of the off modes is executed. In the background mode, the captured image 121 that is sequentially updated is arranged on the left, and a first off indicator 122*c* indicating the off mode and the background mode is arranged on the right. As in the case of the on-mode live display, the captured image 121 that is sequentially updated adopts so-called live display of displaying the captured image captured by the camera unit 210 with substantially no delay. The first off indicator 122*c* is a computer graphic including "OFF" indicating the off mode, and a text "Background Processing" indicating that the diagnosis process is performed in the background, and is one mode of the CG indicator 122. In the background mode, the captured image 121 that is sequentially updated is displayed, and also, an entire display region is shaded in gray, and thus, the off mode and the background mode may be recognized at a glance. A display mode in such an off mode is referred to as off-mode live display.

Figure 3C:
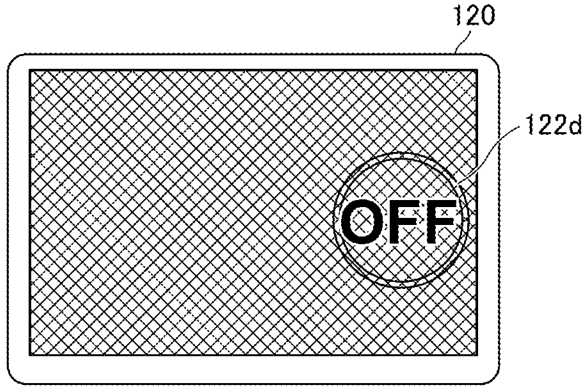

FIG. 3(C) is an example of a display page where the complete off mode of the off modes is executed. In the complete off mode, a second off indicator 122*d* indicating the complete off mode is arranged close to the right side. The second off indicator 122*d* is a computer graphic including a text only "OFF" indicating the off mode, and is one mode of the CG indicator 122. In the complete off mode, the entire display region is shaded in gray without displaying the captured image 121 that is sequentially updated, and the off mode and the complete off mode may be recognized at a glance.

Figure 4:
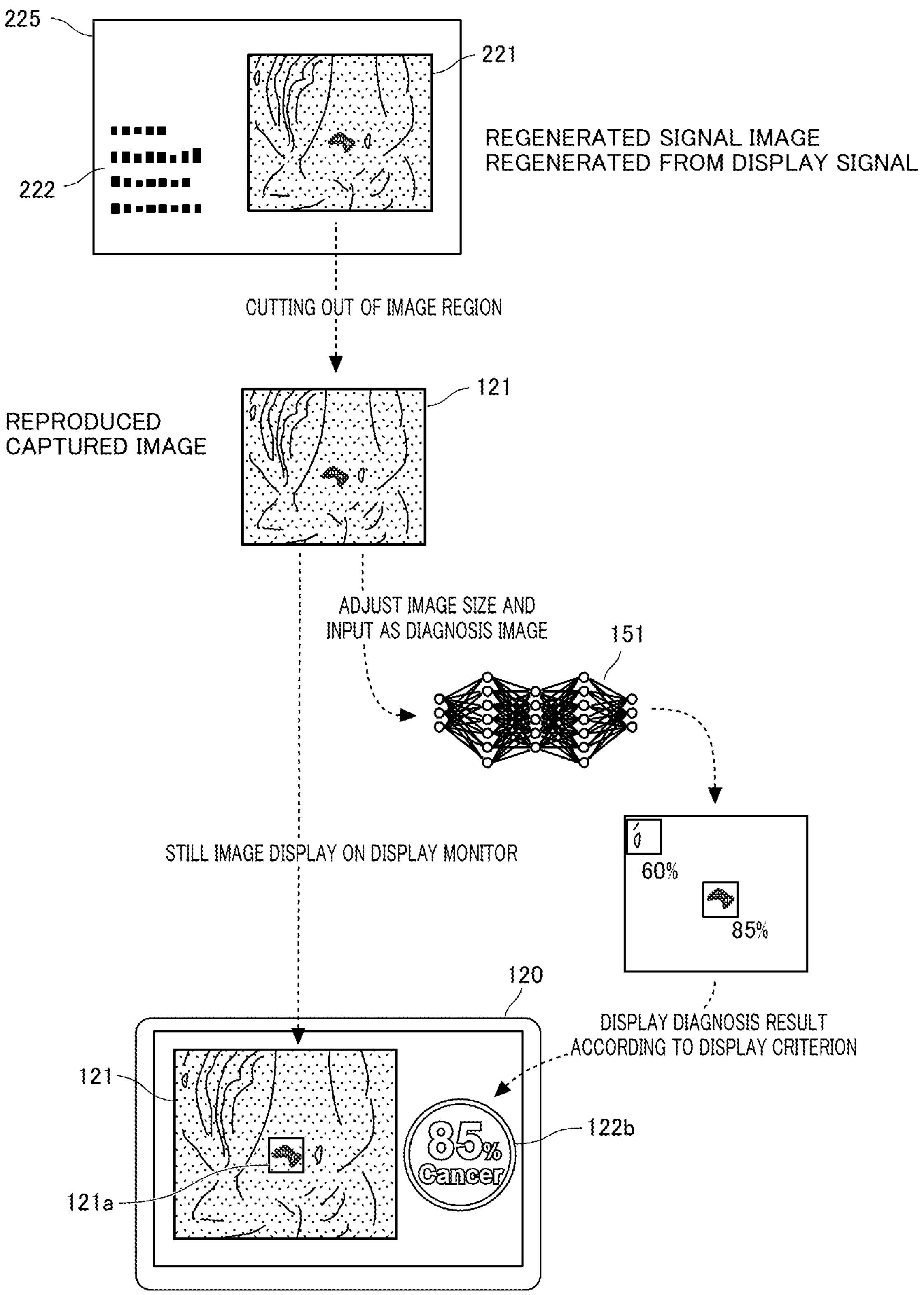
FIG. 4 is a diagram describing a process up to display of a diagnosis result in an on mode.

FIG. 4 is a diagram describing a process up to display of the diagnosis result in the on mode. A regenerated signal image 225 that is obtained by the acquisition unit 111 acquiring and developing a display signal transmitted from the endoscope system 200 is the same as a display image that is displayed on the system monitor 220 of the endoscope system 200. The regenerated signal image 225 includes the captured image 221 and the examination information 222. The examination information 222 is text information, for example.

When which region in an image region of the regenerated signal image 225 is an image region indicating the captured image is established in the above manner, the acquisition unit 111 cuts out the established image region and takes the same as the captured image 121. The captured image 121 can practically be said to be an image that is obtained by reproducing the captured image captured by the camera unit 210 by the examination support device 100.

In the case where the captured image 121 that is cut out is not an image of a diagnosis target, the acquisition unit 111 transfers the captured image 121 to the control unit 113. To obtain the display page in the standby display state described with reference to FIG. 3(A), the control unit 113 sequentially updates the captured image 121 and displays the same on the display monitor 120. In the case where the captured image 121 that is cut out is the image of the diagnosis target, the acquisition unit 111 transfers the captured image 121 to the control unit 113 and to the diagnosis unit 112.

The diagnosis unit 112 adjusts the captured image 121 and generates a diagnosis image according to specifications of the neural network for analysis 151 and the like. Particularly, in the on mode, there is a demand to reduce a delay time until the diagnosis result is displayed as much as possible, and thus, a diagnosis image with a reduced image size obtained by thinning out pixels of the captured image 121 is generated to reduce an amount of calculation by the neural network for analysis 151. Then, the diagnosis unit 112 inputs image data of the diagnosis image that is generated to the neural network for analysis 151, and causes the estimated probability of existence of a lesion in the diagnosis image to be calculated. The neural network for analysis 151 outputs, as a diagnosis result, a region, in the image, where there is a possibility of a lesion together with its estimated probability. In the example in FIG. 4, an upper left region indicating an estimated probability of 60%, and a region near a center indicating an estimated probability of 85% are output. The diagnosis unit 112 transfers the diagnosis result to the control unit 113.

The control unit 113 develops and arranges captured image data of the captured image 121 received from the acquisition unit 111 and the diagnosis result received from the diagnosis unit 112 according to a display criterion set in advance, and displays the same on the display monitor 120. More specifically, display is performed in the mode of the result display state described with reference to FIG. 3(A). As the display criterion, there is a conceivable criterion according to which, in a case where a plurality of lesions are detected in a diagnosis result, one with the highest estimated probability is selected or a lesion that is detected in a region close to a center of the diagnosis image is displayed in a prioritized manner, for example. Furthermore, a display criterion may be set according to which the diagnosis result is not displayed in a case where the diagnosis image that is generated is not clear and the diagnosis result is not credible, or in a case where there is no estimated probability that exceeds a threshold that is set in advance, for example. The display criterion may be set as appropriate according to an observation part, the purpose of the examination, or the like. Furthermore, in the case where a plurality of lesions are detected, it is possible to sequentially switch and display the result indicator 122*b* and the diagnosis region frame 121*a* according to the corresponding lesion.

Figure 5:
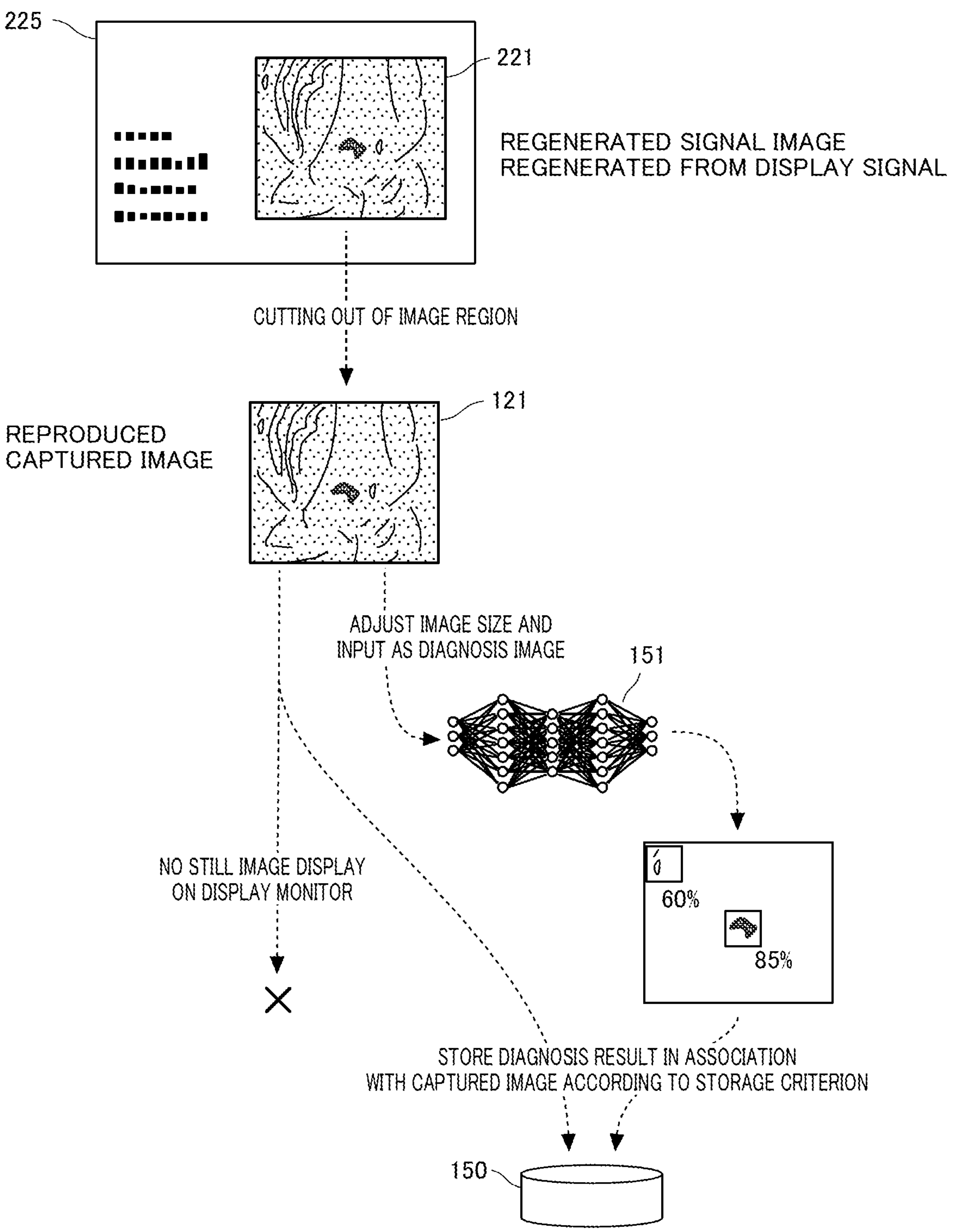
FIG. 5 is a diagram describing a process up to storage of a diagnosis result in a background mode in an off mode.

FIG. 5 is a diagram describing a process up to storage of a diagnosis result in the background mode in the off mode. As in the on mode, the acquisition unit 111 cuts out the captured image 121 from the regenerated signal image 225 obtained by acquiring and developing a display signal transmitted from the endoscope system 200. To obtain the display page in the background mode described with reference to FIG. 3(B), the control unit 113 displays the captured image 121 that is sequentially updated, on the display monitor 120.

In the case where the captured image 121 that is cut out is an image of a diagnosis target, the acquisition unit 111 transfers the captured image 121 to the diagnosis unit 112. The diagnosis unit 112 adjusts the captured image 121 and generates a diagnosis image according to specifications of the neural network for analysis 151 and the like. In the background mode, a diagnosis result does not have to be immediately displayed, and thus, the image size may be adjusted to be greater than the image size in the on mode. That is, a thinning rate for the captured image 121 may be reduced, and a high-definition diagnosis image closer to the captured image 121 may be generated. If processing performance of the arithmetic processing unit 110 is high enough, the captured image 121 may be used as it is as the diagnosis image without being thinned out. If a high-definition diagnosis image is used, diagnosis accuracy may be expected to be increased.

The diagnosis unit 112 inputs image data of the diagnosis image that is generated to the neural network for analysis 151, and causes the estimated probability of existence of a lesion in the diagnosis image to be calculated. The neural network for analysis 151 outputs, as a diagnosis result, a region, in the image, where there is a possibility of a lesion together with its estimated probability. The diagnosis unit 112 transfers the diagnosis result to the control unit 113.

The control unit 113 stores captured image data of the captured image 121 that is received from the acquisition unit 111 and the diagnosis result that is received from the diagnosis unit 112 in the storage unit 150 according to a storage criterion set in advance. Details of the storage criterion will be given later. Additionally, in the on mode, the captured image 121 from which the diagnosis image is generated is displayed as a still image for a specific period of time together with the diagnosis result, but in the background mode, the diagnosis result is not displayed, and thus, the captured image 121 from which the diagnosis image is generated is not displayed as a still image.

In the background mode, when the detection unit 115 detects end of examination of an inside of a body by the camera unit 210, the control unit 113 reads out the diagnosis result stored in the storage unit 150, and causes the same to be displayed on the display monitor 120. For example, the detection unit 115 detects a timing when the camera unit 210 is removed from the mouth, by capturing a drastic change in brightness of the captured image 121. Alternatively, end of an examination may be detected by reading the examination information 222 included in the regenerated signal image 225.

Figure 6:
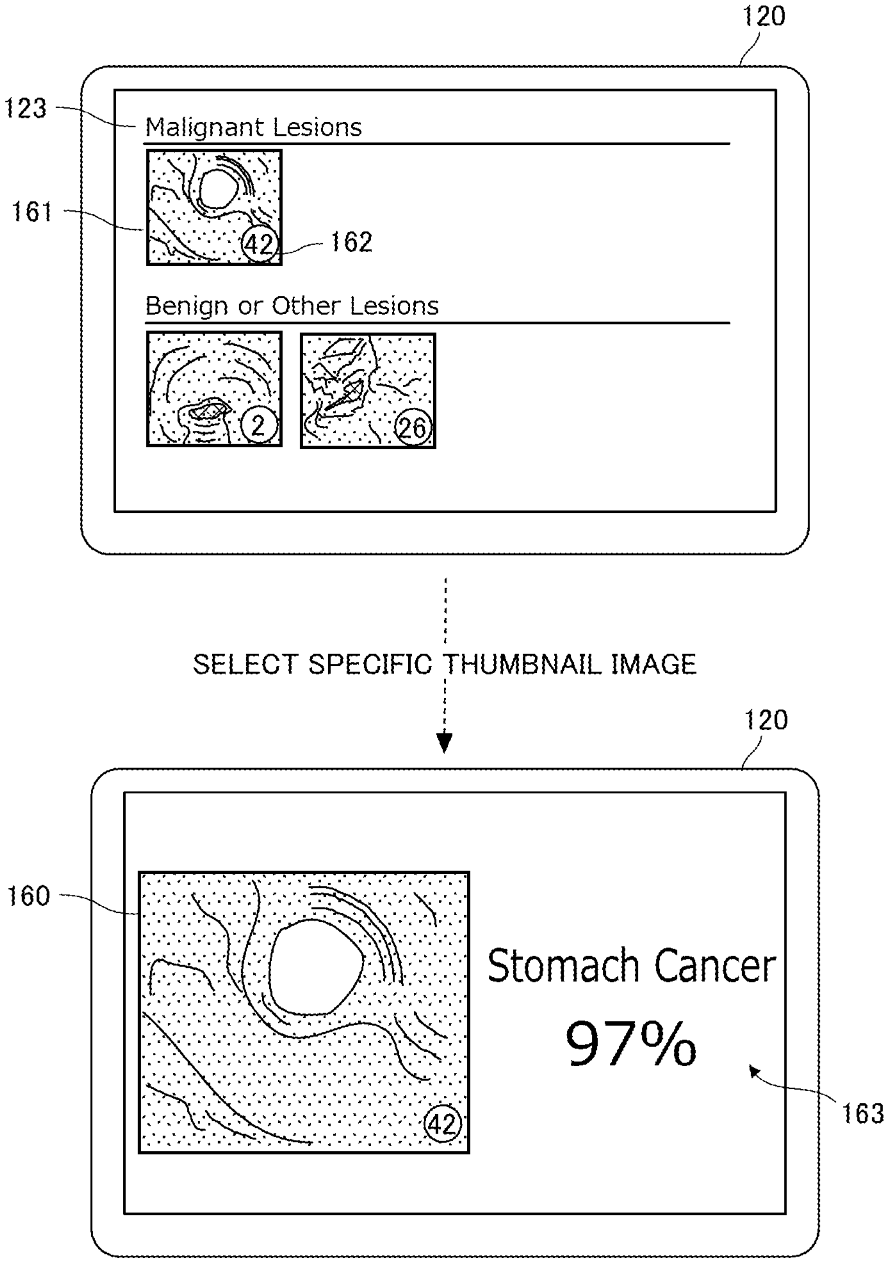
FIG. 6 is a diagram showing an example of a display page for displaying, at the end of an examination, a diagnosis result stored during the examination.

FIG. 6 is a diagram showing an example of a display page for displaying, at the end of an examination, a diagnosis result stored during the examination. In FIG. 6, a top drawing is an example of a display page where diagnosis results that are stored are displayed as thumbnails, and a bottom drawing is an example of a display page when a specific thumbnail image is selected.

The top drawing in FIG. 6 is an example display of a diagnosis result where a storage criterion according to which storing is performed when a lesion is detected is set. That is, the control unit 113 stores the diagnosis result received from the diagnosis unit 112 in the storage unit 150 if the diagnosis result includes lesion detection, and discards the diagnosis result if lesion detection is not included. Then, when end of the examination is detected by the detection unit 115, the control unit 113 reads out diagnosis results that are stored, categorizes the same into "malignant lesions" and "benign or other lesions", and displays thumbnails. More specifically, an image number 162 is superimposed on a thumbnail image 161 that is stored in association with a diagnosis result, and that is cut out, from the captured image 121 which the diagnosis is based on, to include a lesion region. Then, if the diagnosis result indicates a malignant lesion, arranged display is performed under a title 123 "malignant lesions", and if the diagnosis result indicates benign or other lesions, arranged display is performed under a title 123 "benign or other lesions".

When wanting to check a specific thumbnail image 161 in detail, the doctor selects the thumbnail image 161 using the input device 140. When selection of a specific thumbnail image 161 is received, the control unit 113 generates a high-definition image 160 corresponding to the thumbnail image 161 from the original captured image 121, and displays the same on the display monitor 120 in a greater size than the thumbnail image 161 and together with a diagnosis result 163.

Figure 7:
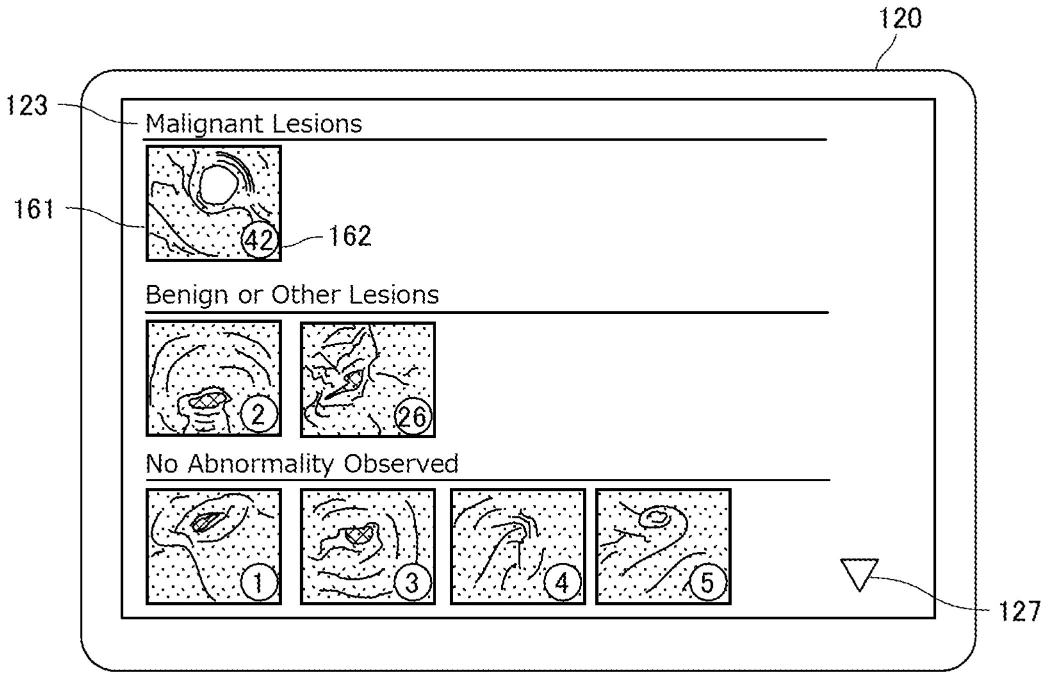
FIG. 7 is a diagram showing another example of the display page for displaying, at the end of an examination, a diagnosis result stored during the examination.

FIG. 7 is a diagram showing another example of the display page for displaying, at the end of an examination, a diagnosis result stored during the examination. More specifically, there is shown an example display of a case where there is set a storage criterion according to which all the diagnosis results obtained by diagnosis by the diagnosis unit 112 are stored. Accordingly, as shown in the drawing, the display page includes a category "no abnormality observed" in addition to "malignant lesions" and "benign or other lesions". In relation to a diagnosis result where no lesion is detected, the control unit 113 superimposes an image number 162 on the thumbnail image 161 of the captured image 121 which the diagnosis is based on, and performs arranged display under a title 123 "no abnormality observed".

A scroll indicator 127 is arranged on lower right of the display page, and in the example in the drawing, it is indicated that thumbnail images 161 for "no abnormality observed" continue below. A doctor may check other thumbnail images 161 by scrolling the display page by selecting the scroll indicator 127. Additionally, as in the example in FIG. 6, when the doctor selects a specific thumbnail image 161, the control unit 113 displays the high-definition image 160 corresponding to the thumbnail image 161 on the display monitor 120 together with the diagnosis result 163.

Additionally, examples in FIG. 6 and FIG. 7 are examples of displaying all the diagnosis results that are stored in the storage unit 150, but it is also possible to select and display one or some of the diagnosis results that are stored in the storage unit 150. That is, a storage criterion regarding storage of the diagnosis result in the storage unit 150 and a selection criterion regarding display on the display monitor 120 at the end of an examination may be different from each other. For example, even in a case where a storage criterion is set such that all the diagnosis results obtained by diagnosis by the diagnosis unit 112 are stored, a selection criterion may be set such that only those for which the estimated probability of estimating that there is a lesion is equal to or greater than a threshold are displayed on the display monitor 120. Additionally, even in a case of a diagnosis result that is not displayed on the display monitor 120 at the end of an examination, or even in a case where it is originally set such that no diagnosis result is to be displayed on the display monitor 120 at the end of an examination, the doctor may freely read out and check a diagnosis result that is stored in the storage unit 150 at the end of the examination.

Figure 8:
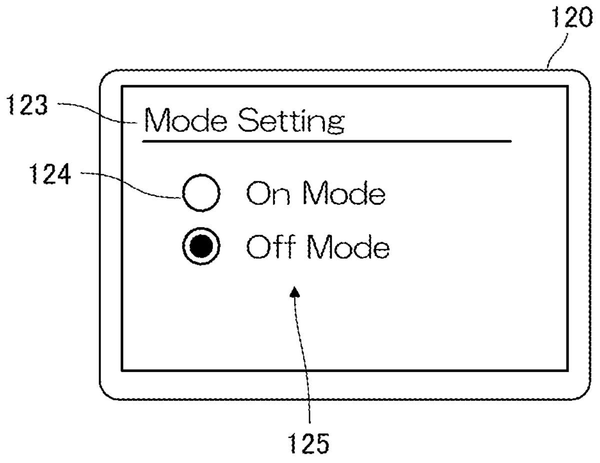
FIG. 8 is a diagram showing an example of a setting page for a mode.

Next, an operation of setting a mode performed by a doctor before start of an examination will be described with reference to several setting pages. The reception unit 114 receives, via the input device 140, selection by a doctor related to mode setting. FIG. 8 is a diagram showing an example of a setting page for a mode. On the setting page for a mode, a title 123 "Mode Setting", selection items 125 "On Mode" and "Off Mode", and a radio button 124 for exclusively specifying and selecting each selection item 125 are arranged. The examination support device 100 operates in the on mode in a case where the reception unit 114 receives selection of "On Mode", and operates in the background mode in the off mode in a case where selection of "Off Mode" is received, unless selection of "complete off" described later is received.

Figure 9:
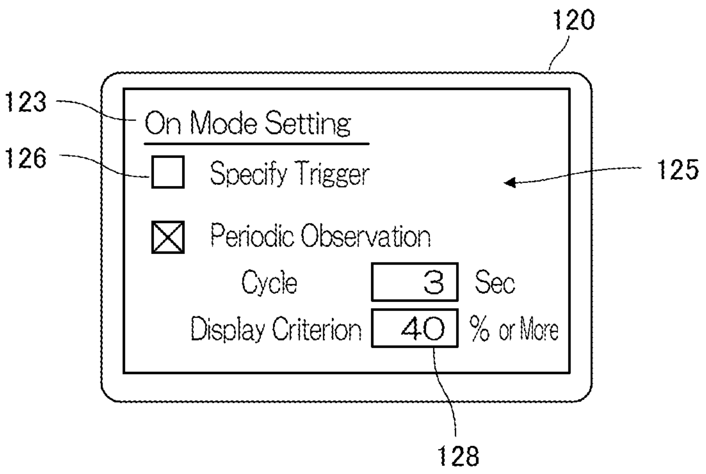
FIG. 9 is a diagram showing an example of a setting page in the on mode.

FIG. 9 is a diagram showing an example of a setting page in the on mode, and is a display page that is a transition destination in a case where "On Mode" is selected on the mode setting page. On the setting page in the on mode, a doctor may set a timing when the diagnosis process is performed by the diagnosis unit 112 in the on mode.

In the example in the drawing, "Specify Trigger" and "Periodic Observation" are displayed in a selectable manner under a title 123 "On Mode Setting", together with respective checkboxes 126. According to "Specify Trigger", when a doctor keeps pressing a still button provided on the endoscope system, for example, the captured image 121 is made a still image, and when the acquisition unit 111 detects such a still image period, this is taken as a trigger for the diagnosis unit 112 to start the diagnosis process. That is, it is set such that the diagnosis process is started when it is determined that diagnosis is required by the doctor. Accordingly, in a case where "Specify Trigger" is selected, the diagnosis result is desirably displayed with no exception regardless of the contents.

In "Periodic Observation", the diagnosis process is continuously performed according to a cycle that is set. In relation to the setting "Periodic Observation", input boxes 128 "Cycle" and "Display Criterion" are provided, and a cycle (seconds) of performance of the diagnosis process and a threshold (%) for the estimated probability regarding whether to display the diagnosis result or not may be respectively set. In the example in the drawing, it is set such that the diagnosis process is performed every three seconds, and such that the diagnosis result is displayed in a case where there is a lesion part, in the diagnosis result, for which the estimated probability is calculated to be 40% or more. Additionally, when selecting the checkboxes 126 of both "Specify Trigger" and "Periodic Observation", the doctor may cause the diagnosis process to be performed both based on the trigger from the doctor and at the cycle that is set.

Figure 10:
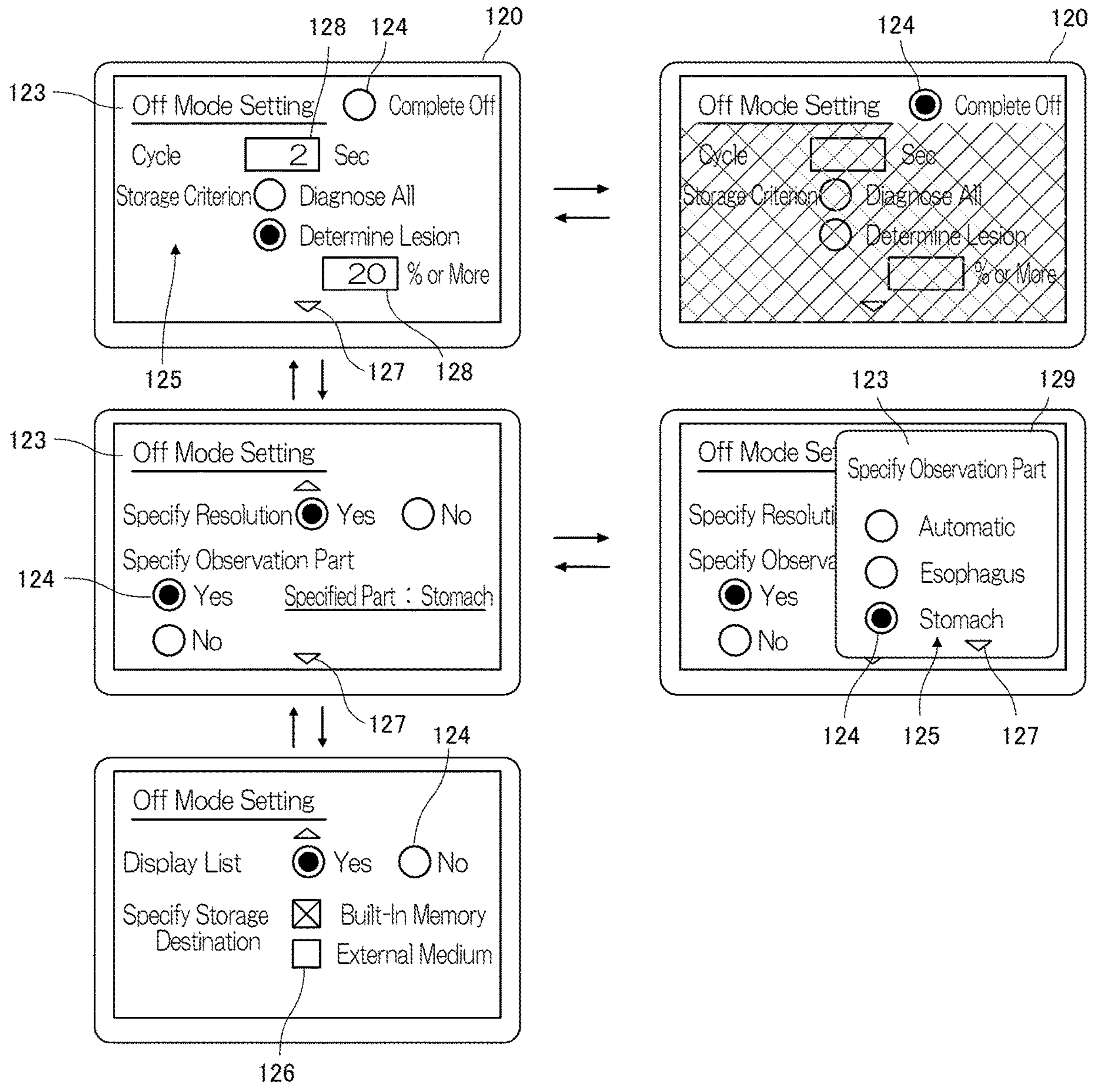
FIG. 10 is a diagram showing an example of a setting page in the off mode.

FIG. 10 is a diagram showing an example of a setting page in the off mode, and is a display page that is a transition destination in a case where "Off Mode" is selected on the mode setting page. When "Off Mode" is selected on the mode setting page, first, a transition to a setting page on the top left takes place. In the setting page on the top left, a radio button 124 for selecting the complete off mode, selection items 125 regarding the cycle and the storage criterion in the case of operation in the background mode, and an input box 128 are arranged together with a title 123 "Off Mode Setting".

When the radio button 124 "Complete Off" is selected, a transition to a display page on the top right takes place. In the complete off mode, a region regarding setting related to the background mode is displayed while being shaded. The complete off mode has to be more consciously selected because, in this mode, the diagnosis process is not performed by the diagnosis unit 112 and the diagnosis result cannot be reviewed after end of the examination. Accordingly, in an initial setting, it is set such that the background mode is first set when the off mode is selected, and such that selection of the complete off mode is received in a layer deeper than a layer where the background mode is set. By adopting such a user interface, the doctor is prevented from inadvertently selecting the complete off mode.

The display page on the top left will be referred to again. In the background mode, the doctor can set a cycle at which the diagnosis process by the diagnosis unit 112 is performed. For example, when "2" seconds is input in the input box 128 as shown in the diagram, the diagnosis unit 112 generates a diagnosis image and performs the diagnosis process every two seconds. In this manner, the cycle in the background mode may be made different from the cycle in the case of performing periodic observation in the on mode. That is, a proportion of performance of the diagnosis process by the diagnosis unit 112 on the captured image 121 acquired by the acquisition unit 111 may be changed. Real-time display of the diagnosis result in the on mode has an aspect that interrupts progress of the examination, and thus, it can be said that it is better to reduce frequency of the diagnosis process. In contrast, in the background mode in the off mode, progress of the examination is not interrupted, and thus, the diagnosis process may be performed more often. In this manner, convenience of the examination support device 100 may be increased by changing, if possible, the proportion of performance of the diagnosis process as appropriate according to the state of the examination.

Moreover, the doctor is allowed to set the storage criterion. The storage criterion is a criterion set for at least one of the captured image and the diagnosis result, and the control unit 113 causes a diagnosis result to be stored in the storage unit 150 when the storage criterion that is set is satisfied. In relation to the storage criterion, first, it is possible to select one of a case where all the diagnosis results obtained by performing the diagnosis process are stored, and a case where only the diagnosis result indicating an estimated probability equal to or greater than a threshold is stored. A value of the threshold for the estimated probability may be specified using an input box 128. If only the diagnosis result indicating an estimated probability equal to or greater than the threshold is stored, work may be reduced at a time when the doctor checks the diagnosis result after the examination. On the other hand, the threshold for the estimated probability set as the storage criterion may be set to a small value compared with the threshold for the estimated probability set as the display criterion in the on mode. In the background mode, real-time display of the examination result is not performed, and thus, progress of the examination can not obstructed even when the threshold for the estimated probability is set to a small value. In this manner, even in the case of setting items that are related to each other, the display criterion and the storage criterion may be made different according to respective properties.

When the scroll indicator 127 is selected on the display page on the top left, a transition to a display page on the middle left takes place, and the doctor is able to set the storage criterion for the captured image. In the example in the drawing, "Specify Resolution" and "Specify Observation Part" may be set. "Specify Resolution" is for specifying that the diagnosis process is performed only when the captured image 121 acquired by the acquisition unit 111 is a high-resolution image. Such a restriction is applied when a radio button 124 "Yes" is selected, and the diagnosis process is performed with no restriction when a radio button 124 "No" is selected. For example, the resolution is evaluated based on high-frequency components included in the captured image 121, and "high resolution" is determined in a case where a proportion of high-frequency components is equal to or greater than a threshold that is set in advance. When the captured image 121 as an original image based on which the diagnosis image is generated is limited to a high-resolution image, reliability of the estimated probability output by the neural network for analysis 151 is also increased.

Additionally, with respect to the storage criterion regarding the captured image 121, whether the captured image 121 satisfies the storage criterion or not may be determined at the time point of storing the diagnosis result in the storage unit 150, or whether the storage criterion is satisfied or not may be determined at the time point of acquisition of the captured image 121 by the acquisition unit 111. In the case where determination is to be performed at the time point of storing the diagnosis result in the storage unit 150, if it is determined that storage is not to be performed in the first place according to another storage criterion (for example, the threshold for the estimated probability), calculation of evaluation of resolution or the like for the captured image may be omitted. In the case where determination is to be performed at the time point of acquisition of the captured image 121 by the acquisition unit 111, the diagnosis process by the diagnosis unit 112 may be omitted.

"Specify Observation Part" is for specifying that the diagnosis process is to be performed only in the case where the captured image 121 that is acquired by the acquisition unit 111 is an image of an observation part that is specified. That is, the diagnosis part is limited to a specific organ. Such a restriction is applied in the case where a radio button 124 "Yes" is selected, and the diagnosis process is performed with no restriction in the case where a radio button 124 "No" is selected. In the case where "Yes" is selected, a window 129 for specifying the observation part appears as shown in a diagram on the middle right.

The window 129 includes a title 123 "Specify Observation Part", a selection item 125 indicating an observation part, a radio button 124 allowing exclusive selection of each selection item, and a scroll indicator 127. As the selection items 125, "Automatic", "Esophagus", "Stomach", and the like are prepared. In "Automatic", for example, whether or not the neural network for analysis 151 that is prepared is a learning model that takes a specific observation part as a target is checked, and in the case of the learning model that takes the specific observation part as the target, the observation part in question is taken as a specified part. Alternatively, in the case where an observation part is specified by the endoscope system 200, if character information regarding the observation part is included in the examination information 222 in the regenerated signal image 225, the character information is read and the observation part is taken as the specified part. In the case where a specific observation part such as "Esophagus" or "Stomach" is specified, such specification is followed. When an observation part is specified in the window 129, a transition to the display page on the middle left takes place, and a text of the specified observation part appears in the manner of "Specified Part: Stomach".

When an observation part is specified in this manner, the diagnosis unit 112 determines whether the captured image 121 transferred from the acquisition unit 111 is that obtained by capturing the observation part that is set. Then, the control unit 113 causes the diagnosis result to be stored in the storage unit 150 only when capturing of the observation part that is set is determined by the diagnosis unit 112. Additionally, the diagnosis unit 112 may determine, before the diagnosis process, whether the captured image 121 transferred from the acquisition unit 111 is that obtained by capturing the observation part that is set or not, and does not have to perform the diagnosis process in the case where other than the observation part that is set is determined. In the case of determining whether the captured image 121 transferred from the acquisition unit 111 is that obtained by capturing the observation part that is set or not, the diagnosis unit 112 may use a neural network for part determination that is prepared separately from the neural network for analysis 151. For example, in the case where "Stomach" is specified as the observation part, the diagnosis unit 112 performs determination regarding the captured image 121 transferred from the acquisition unit 111, using the neural network for part determination that outputs a probability of an input image being the stomach. Then, the captured image is input to the neural network for analysis 151 and the diagnosis process is performed only in the case where the probability that is output by the neural network for part determination is equal to or greater than a threshold.

When the scroll indicator 127 is selected on the display page on the middle left, a transition to a display page on the bottom left takes place. The display page on the bottom left is related to settings related to list display at the end of the examination and storage destination of the diagnosis result. "Display List" is for specifying whether to display diagnosis results in a list at the end of the examination by using thumbnail display described with reference to FIGS. 6 and 7. List display is performed when a radio button 124 "Yes" is selected, and list display is not performed when a radio button 124 "No" is selected. "Specify Storage Destination" is for specifying a storage medium where the diagnosis result is to be stored. Heretofore, a description has been given assuming that the diagnosis result is stored in the storage unit 150, which is a built-in memory, but the storage destination does not have to be the storage unit 150. An external medium may also be specified. The external medium may be a cloud server connected to a network, for example. In the case where a checkbox 126 for an external medium is selected, a setting page for setting an IP address may be shown.

Figure 11:
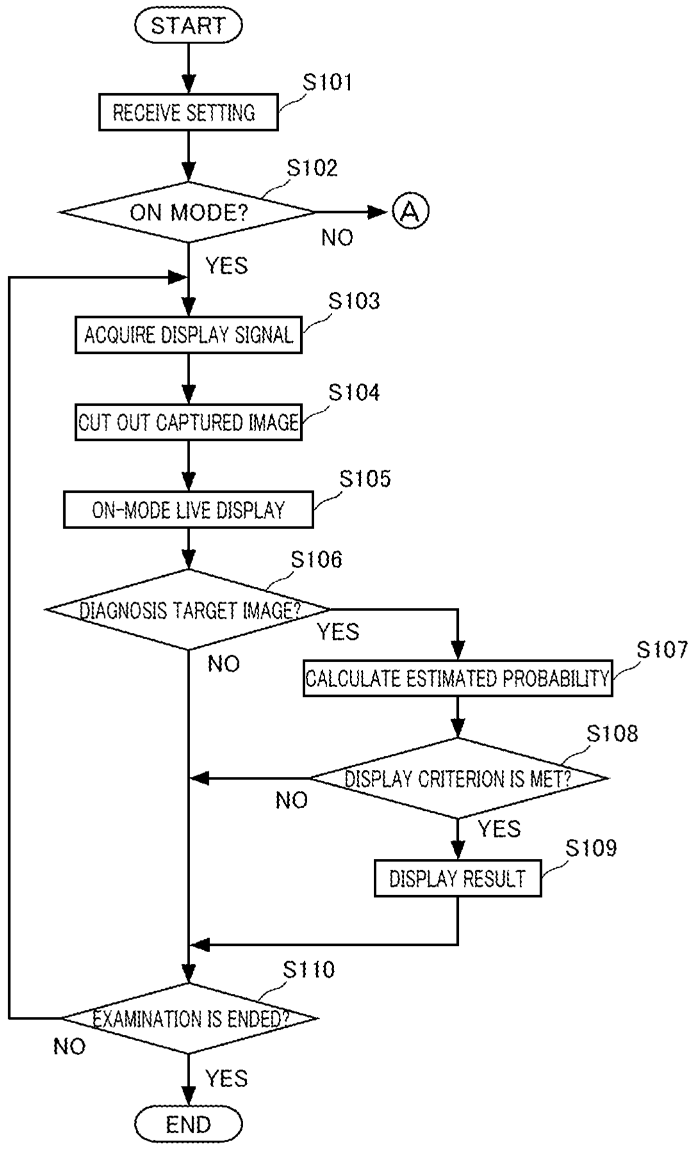
FIG. 11 is a flowchart describing a processing procedure of an arithmetic processing unit, where the flowchart mainly describes the processing procedure where the on mode is set.

Next, an example of a processing procedure of main processes performed by the arithmetic processing unit 110 will be described with reference to a flowchart. FIG. 11 is a flowchart describing a processing procedure of the arithmetic processing unit 110, where the flowchart mainly describes the processing procedure where the on mode is set. The flow is started when the examination support device 100 is activated and the examination support program is executed.

In step S101, the reception unit 114 receives various settings from the doctor via the input device 140. The doctor performs setting according to the purpose of the examination, via the user interfaces described with reference to FIGS. 8 to 10. When reception of the settings is complete, step S102 is performed next.

Figure 12:
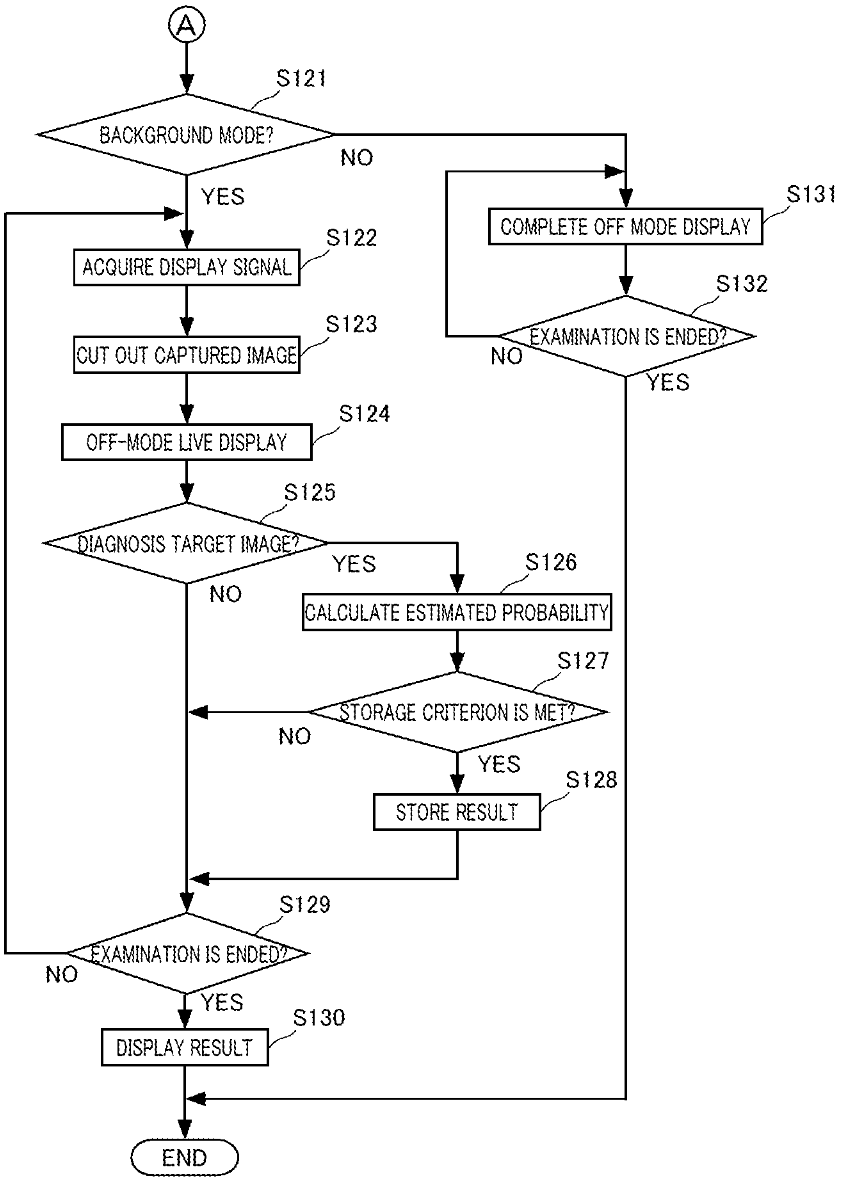
FIG. 12 is a flowchart describing a processing procedure of the arithmetic processing unit, where the flowchart mainly describes the processing procedure where the off mode is set.

In step S102, the control unit 113 checks whether the on mode is set or the off mode is set. When the on mode is set, step S103 is performed next, and when the off mode is set, step S121 in FIG. 12 is performed next. Here, a case where the on mode is set is first described.

When proceeding to step S103, the acquisition unit 111 acquires a display signal from the endoscope system 200, generates the regenerated signal image 225, and then, cuts out the captured image 121 from the regenerated signal image 225 in step S104 and transfers the same to the control unit 113. In step S105, the control unit 113 performs on-mode live display of sequentially updating and displaying the captured image 121 on the display monitor 120 as in the example in the left diagram in FIG. 3(A).

In step S106, the acquisition unit 111 determines whether the captured image 121 that is generated is a diagnosis target image or not. For example, in the case where specification of trigger is set, whether the captured image 121 that is generated is in a still image state continuously for a specific period of time or not is determined. In the case where the diagnosis target image is determined, the captured image 121 is transferred to the diagnosis unit 112 and step S107 is performed next, and in the case where the diagnosis target image is not determined, step S110 is performed next.

When proceeding to step S107, the diagnosis unit 112 generates a diagnosis image from the captured image 121 transferred from the acquisition unit 111, and performs the diagnosis process. More specifically, a region that possibly includes a lesion and its estimated probability are calculated using the neural network for analysis 151. Then, the diagnosis result is transferred to the control unit 113. In step S108, the control unit 113 determines whether the diagnosis result that is received meets the display criterion that is set in step S101 or that is specified in advance.

For example, when the display criterion is specified to be 40% or more in the case where the on mode is being performed under periodic observation, the display criterion is determined to be met when the estimated probability included in the diagnosis result is 40% or more, and the display criterion is not determined to be met when the estimated probability is less than 40%. In the case where it is determined that the display criterion is not met, step S110 is performed next without displaying the diagnosis result. In the case where it is determined that the display criterion is met, step S109 is performed next, and the control unit 113 displays the diagnosis result in the manner of the right diagram in FIG. 3(A). Then, after the state of result display is maintained for a specific period of time, step S110 is performed next.

In step S110, the detection unit 115 detects whether the in-body examination by the camera unit 210 is ended or not. When end is not detected, step S103 is performed again, and the examination is continued in the on mode. When end is detected, a specified end process is performed, and the series of processes are ended.

FIG. 12 is a flowchart describing a processing procedure of the arithmetic processing unit 110, where the flowchart mainly describes the processing procedure where the off mode is set and is a flow following step S102 in FIG. 11.

In step S121, the control unit 113 checks whether the background mode is set or the complete off mode is set. When the background mode is set, step S122 is performed next, and when the complete off mode is set, step S131 is performed next.

When proceeding to step S122, the acquisition unit 111 acquires a display signal from the endoscope system 200, generates the regenerated signal image 225, and then, cuts out the captured image 121 from the regenerated signal image 225 in step S123 and transfers the same to the control unit 113. In step S124, the control unit 113 performs off-mode live display of sequentially updating and displaying the captured image 121 on the display monitor 120 while applying shading as in the example in FIG. 3(B).

In step S125, the acquisition unit 111 determines whether the captured image 121 that is generated is a diagnosis target image or not. For example, in the case where the cycle is set to two seconds, whether the captured image 121 that is generated matches the timing or not is determined. Furthermore, in the case where an observation part is specified, the acquisition unit 111 transfers the captured image 121 to the diagnosis unit 112 such that whether a part that is shown in the captured image 121 is the observation part that is specified is determined. In the case where the diagnosis target image is determined, the captured image 121 is transferred to the diagnosis unit 112 and step S126 is performed next, and in the case where the diagnosis target image is not determined, step S129 is performed next.

When proceeding to step S126, the diagnosis unit 112 generates a diagnosis image from the captured image 121 transferred from the acquisition unit 111, and performs the diagnosis process. More specifically, a region that possibly includes a lesion and its estimated probability are calculated using the neural network for analysis 151. Then, the diagnosis result is transferred to the control unit 113. In step S127, the control unit 113 determines whether the diagnosis result that is received meets the storage criterion that is set in step S101 or that is specified in advance.

For example, in the case where the captured image 121 that is an original image of the diagnosis image is determined not to have a high resolution when specification of resolution is set to "Yes", it is determined that the storage criterion is not met. In the case where the storage criterion is not determined to be met, the diagnosis result is not stored, and step S129 is performed next. In the case where the storage criterion is determined to be met, step S128 is performed next, and the control unit 113 stores the diagnosis result in a storage unit such as the storage unit 150. When the storage process is complete, step S129 is performed next.

In step S129, the detection unit 115 detects whether the in-body examination by the camera unit 210 is ended or not. When end is not detected, step S122 is performed again, and the examination is continued in the background mode. When end is detected, step S130 is performed next.

When proceeding to step S130, the control unit 113 reads out the diagnosis result that is stored in the storage unit, and causes the same to be displayed on the display monitor 120 as in the example in FIG. 6 or 7. Then, when an instruction to end display is received by the reception unit 114, a specified end process is performed, and the series of processes are ended.

When proceeding from step S121 to step S131, the control unit 113 performs display in the complete off mode as in FIG. 3(C). Step S131 is regularly performed while display is being performed in the complete off mode, and the detection unit 115 detects whether the in-body examination by the camera unit 210 is ended or not. When end is not detected, step S131 is performed again, and display in the complete off mode is continued. When end is detected, a specified end process is performed, and the series of processes are ended.

Heretofore, the present embodiment has been described, but the user interfaces described herein are merely examples and are not restrictive, and any mode is allowed as long as reception of various setting items and provision of information are enabled. For example, audio input that recognizes voice of the doctor as a user, or augmented reality (AR) technology of superimposing provision information on wearable glasses may be adopted. Moreover, the setting items above are merely examples, and may be selected as appropriate according to specifications and the like of an examination device.

Furthermore, as a modification of the present embodiment, it is also possible to adopt an embodiment as follows, namely, an embodiment in which the background mode is also executed in parallel when executing the on mode in the embodiment described above. For example, in relation to a diagnosis process that is performed when a diagnosis trigger from the doctor is detected, there is a demand to reduce a delay time until the diagnosis result is displayed as much as possible, and thus, a diagnosis image, an image size of which is reduced by greatly thinning out the pixels of the captured image 121, is used. However, in relation to a periodical diagnosis process where the diagnosis result is checked after end of the examination and thus, is not displayed during the examination, securing of diagnosis accuracy is prioritized, and a diagnosis image, an image size of which is reduced without greatly thinning out pixels of the captured image 121, is used.

Convenience of the examination support device may be increased by executing, in parallel, a calculation process for a diagnosis result that is to be displayed in real time on the display monitor 120 (a first diagnosis process), and a calculation process that is for a diagnosis result that is stored in the storage unit during the examination without being displayed on the display unit, and that requires a greater amount of calculation (a second diagnosis process). A configuration of such an examination support device can be as follows.

<Configuration of Another Mode>

An examination support device that is used by being connected to an endoscope system including a camera unit for being inserted into an inside of a body of a subject, the examination support device including:

- an acquisition unit for sequentially acquiring a captured image that is captured by the camera unit;
- a diagnosis unit for performing diagnosis of the inside of the body based on the captured image; and
- a display unit for displaying a diagnosis result that is output by the diagnosis unit, where
- the diagnosis unit performs a first diagnosis process for causing the diagnosis result to be displayed on the display unit in real time during examination of the inside of the body, and a second diagnosis process for presenting the diagnosis result after examination of the inside of the body, and
- an amount of calculation is greater for the second diagnosis process than for the first diagnosis process.

Such an examination support device may satisfy both a demand to swiftly check the diagnosis result even during an examination, and a demand to obtain a highly accurate diagnosis result. To obtain a highly accurate diagnosis result, the amount of calculation is increased and a processing time is increased for that, but when the captured image 121 as the diagnosis target can at least be acquired, the diagnosis process can be accomplished due to there being no restriction of real-time display. The process for obtaining a highly accurate diagnosis result does not depend solely on the amount of thinning for the diagnosis image, and switching of the neural network for analysis to be used may also be adopted, for example. More specifically, there may be prepared a first neural network for the first diagnosis process that places a higher priority on a calculation speed than on accuracy, and a second neural network for the second diagnosis process that places a higher priority on the accuracy than on the calculation speed.

Additionally, the storage criterion and the display criterion described above may be set also in an embodiment according to such a modification. In the embodiment described above, setting is received based on the mode "on mode" or "off mode", but setting may instead be received in relation to "first diagnosis process" or "second diagnosis process". In this case, specification of the resolution or the observation part may be received in relation to the second diagnosis process, for example.

In the present embodiment described above, a case is assumed where the endoscope system 200 and the examination support device 100 are connected by the connection cable 250, but wireless connection may also be adopted instead of wired connection. Furthermore, an embodiment is described where the endoscope system 200 outputs a display signal to outside, and the examination support device 100 uses the display signal, but the format of an output signal is not particularly specified as long as an image signal that is provided to an external device by the endoscope system 200 includes an image signal of a captured image that is captured by the camera unit 210. Moreover, in the present embodiment described above, a description is given assuming that the camera unit 210 of the endoscope system 200 is a flexible endoscope, but the configuration and processing procedures of the examination support device 100 are no different even when the camera unit 210 is a rigid endoscope. Additionally, diagnosis by the diagnosis unit in the present embodiment is only for aiding diagnosis by the doctor, and final decision is made by the doctor.

REFERENCE SIGNS LIST

100 examination support device
110 arithmetic processing unit
111 acquisition unit
112 diagnosis unit
113 control unit
114 reception unit
115 detection unit
120 display monitor
121 captured image
121*a* diagnosis region frame
122 CG indicator
122*a* standby indicator
122*b* result indicator
122*c* first off indicator
122*d* second off indicator
123 title
124 radio button
125 selection item
126 checkbox
127 scroll indicator
128 input box
129 window
130 input/output interface
140 input device
150 storage unit
151 neural network for analysis
160 high-definition image
161 thumbnail image
162 image number
163 diagnosis result
200 endoscope system
210 camera unit
220 system monitor
221 captured image
222 examination information
225 regenerated signal image
250 connection cable

The invention claimed is:

1. An examination support device that is used by being connected to an endoscope system including a camera for being inserted into an inside of a body of a subject, the examination support device comprising:

a processor coupled to a memory storing instructions and configured to execute instructions to:

sequentially acquire a captured image that is captured by the camera;

perform diagnosis of the inside of the body based on the captured image;

display a diagnosis result that is output by the processor;

receive, from a user, selection of an on mode in which the diagnosis result is displayed on a display or an off mode in which display is not performed; and cause the diagnosis result to be displayed on the display in real time in a case where selection of the on mode is received by the processor, and causing the diagnosis result to be stored in a storage unit without being displayed on the display at least while examination of the inside of the body by the camera is being performed, in a case where selection of the off mode is received, wherein the processor causes a frequency of performing the diagnosis on the captured image acquired by the processor to be different between a case where selection of the on mode is received by the processor and a case where selection of the off mode is received.

2. The examination support device according to claim 1, wherein, in a case where selection of the off mode is received, the processor causes the diagnosis result to be stored in the storage unit in a case where a storage criterion that is set in advance in relation to at least one of the captured image and the diagnosis result is satisfied.

3. The examination support device according to claim 2, wherein the storage criterion includes an estimated probability of estimating that there is a lesion included in the diagnosis result being equal to or greater than a threshold.

4. The examination support device according to claim 2, wherein the storage criterion includes a resolution of the captured image being equal to or greater than a threshold.

5. The examination support device according to claim 2, wherein the processor receives setting of the storage criterion from the user.

6. The examination support device according to claim 2, wherein, when selection of the on mode is received by the processor, in a case where a display criterion set in advance for at least one of the captured image and the diagnosis result is satisfied, the processor causes the diagnosis result to be displayed on the display for a predetermined period of time together with the captured image used by the processor—for the diagnosis.

7. The examination support device according to claim 6, wherein the storage criterion and the display criterion are different from each other.

8. The examination support device according to claim 1, wherein the processor determines whether the captured image acquired by the processor depicts a predetermined anatomical observation part, and in a case where selection of the off mode is received, the processor causes the diagnosis result to be stored in the storage unit when capturing of the diagnosis part is determined by the processor.

9. The examination support device according to claim 8, wherein the diagnosis part is set based on a learning model that is used by the processor.

10. The examination support device according to claim 8, wherein the diagnosis part is set based on examination information included in a regenerated signal image from the endoscope system.

11. The examination support device according to claim 1, wherein the processor executes detecting end of examination of the inside of the body by the camera, and wherein, in a case where selection of the off mode is received, the processor reads out the diagnosis result stored in the storage unit and causes the diagnosis result to be displayed on the display after the end of the examination is detected by the processor.

12. The examination support device according to claim 11, wherein the processor selectively displays only diagnosis results where an estimated probability of estimating that there is a lesion is equal to or greater than a threshold to be displayed on the display.

13. The examination support device according to claim 1, wherein the processor performs reception regarding the off mode while distinguishing between a background mode and a complete off mode, and the processor causes the diagnosis result to be stored in the storage unit without being displayed on the display in a case where selection of the background mode is received by the processor, and does not cause the processor to perform the diagnosis in a case where selection of the complete off mode is received.

14. The examination support device according to claim 13, wherein the processor receives selection of the complete off mode through a user interface requiring additional selection steps beyond selecting the background mode.

15. The examination support device according to claim 13, wherein the processor displays a notice indicating the off mode on the display so that the background mode and the complete off mode are visually distinguishable from each other.

16. The examination support device according to claim 1, wherein the frequency of performing the diagnosis in a case where selection of the off mode is received is lower than the frequency of performing the diagnosis in a case where selection of the on mode is received.

17. The examination support device according to claim 1, wherein, in a case where selection of the off mode is received, the processor performs the diagnosis on a subset of the captured images sequentially acquired by the processor.

18. The examination support device according to claim 1, wherein the processor stored in the storage unit is stored in association with the captured image used by the processor for the diagnosis.

19. An examination support method performed using the examination support device according to claim 1, the examination support method comprising:

receiving, from the user, selection of the on mode in which the diagnosis result is displayed on the display or the off mode in which display is not performed;

sequentially acquiring the captured image that is captured by the camera;

performing diagnosis of the inside of the body based on the captured image;

causing the diagnosis result to be displayed in real time on the display in a case where selection of the on mode is received;

causing the diagnosis result to be stored in the storage unit without being displayed on the display at least while examination of the inside of the body by the camera is being performed, in a case where selection of the off mode is received from the user, and causing the frequency of performing the diagnosis on the captured image to be different between the case where selection of the on mode is received and the case where selection of the off mode is received.

20. A storage medium storing an examination support program for controlling the examination support device according to claim 1, the examination support program being for causing a computer to perform:

receiving, from the user, selection of the on mode in which the diagnosis result is displayed on the display or the off mode in which display is not performed;

sequentially acquiring the captured image that is captured by the camera;

performing diagnosis of the inside of the body based on the captured image;

causing the diagnosis result to be displayed in real time on the display in a case where selection of the on mode is received;

causing the diagnosis result to be stored in the storage unit without being displayed on the display at least while examination of the inside of the body by the camera is being performed, in a case where selection of the off mode is received from the user, and causing the frequency of performing the diagnosis on the captured image to be different between the case where selection of the on mode is received and the case where selection of the off mode is received.

* * * * *